United States Patent
To et al.

(10) Patent No.: US 11,441,198 B2
(45) Date of Patent: Sep. 13, 2022

(54) COMPOSITIONS AND METHODS FOR PROVIDING A PROGNOSIS FOR INFLUENZA INFECTION

(71) Applicant: VERSITECH LIMITED

(72) Inventors: Kai Wang Kelvin To, Pokfulam (HK); Jie Zhou, Pokfulam (HK); Johnson Yiu-Nam Lau, Houston, TX (US); Kwok-Yung Yuen, Pokfulam (HK)

(73) Assignee: VERSITECH LIMITED, Hong Kong (CN)

( * ) Notice: Subject to any disclaimer, the term of this patent is extended or adjusted under 35 U.S.C. 154(b) by 476 days.

(21) Appl. No.: 16/312,958

(22) PCT Filed: Jun. 30, 2017

(86) PCT No.: PCT/US2017/040368
§ 371 (c)(1),
(2) Date: Dec. 21, 2018

(87) PCT Pub. No.: WO2018/006014
PCT Pub. Date: Jan. 4, 2018

(65) Prior Publication Data
US 2019/0323094 A1    Oct. 24, 2019

Related U.S. Application Data

(60) Provisional application No. 62/357,569, filed on Jul. 1, 2016.

(51) Int. Cl.
| | | |
|---|---|---|
| *C12Q 1/68* | (2018.01) | |
| *C12Q 1/70* | (2006.01) | |
| *G16B 20/20* | (2019.01) | |
| *G16H 50/20* | (2018.01) | |
| *C12Q 1/6883* | (2018.01) | |
| *G01N 33/569* | (2006.01) | |
| *G16H 50/30* | (2018.01) | |

(52) U.S. Cl.
CPC .......... *C12Q 1/70* (2013.01); *C12Q 1/6883* (2013.01); *C12Q 1/701* (2013.01); *G16B 20/20* (2019.02); *G16H 50/20* (2018.01); *C12Q 2600/118* (2013.01); *C12Q 2600/156* (2013.01); *G01N 33/56983* (2013.01); *G01N 2333/11* (2013.01); *G01N 2800/52* (2013.01); *G16H 50/30* (2018.01)

(58) Field of Classification Search
None
See application file for complete search history.

(56) References Cited

U.S. PATENT DOCUMENTS

2013/0203827 A1    8/2013   Sucharov et al.

FOREIGN PATENT DOCUMENTS

| WO | 2004071377 | 8/2004 |
| WO | 2008157518 | 12/2008 |

OTHER PUBLICATIONS

PCT Search Report & Written Opinion dated Sep. 20, 2017 for PCT/US2017/040368 filed on Jun. 30, 2017 entitled Compositions and Methods for Providing a Prognosis for Influenza Infection (15 pages).
Davey et al, The Association between Serum Biomarkers and Disease Outcome in Influenza A(H1N1)pdm09 Virus Infection: Results of Two International Observational Cohort Studies; PLOS One, Feb. 2013, vol. 8, Issue 2.
Zhou et al, A Functional Variation in CD55 Increases the Severity of 2009 Pandemic H1N1 Influenza a Virus Infection; JID; Aug. 15, 2012; pp. 499-503.

*Primary Examiner* — Jehanne S Sitton
(74) *Attorney, Agent, or Firm* — Pabst Patent Group LLP

(57) ABSTRACT

Compositions and methods are described that provide prognostic determination of the severity of influenza infection based on the PDE3A status of an individual. Impaired PDE3A function is associated with severe symptoms on contracting influenza. Specific SNP mutations are identified that are associated with impaired PDE3A function, and primers and kits are provided that permit identification of these SNPs. Such information can also be combined with other patient data.

12 Claims, 7 Drawing Sheets

Figure 1:
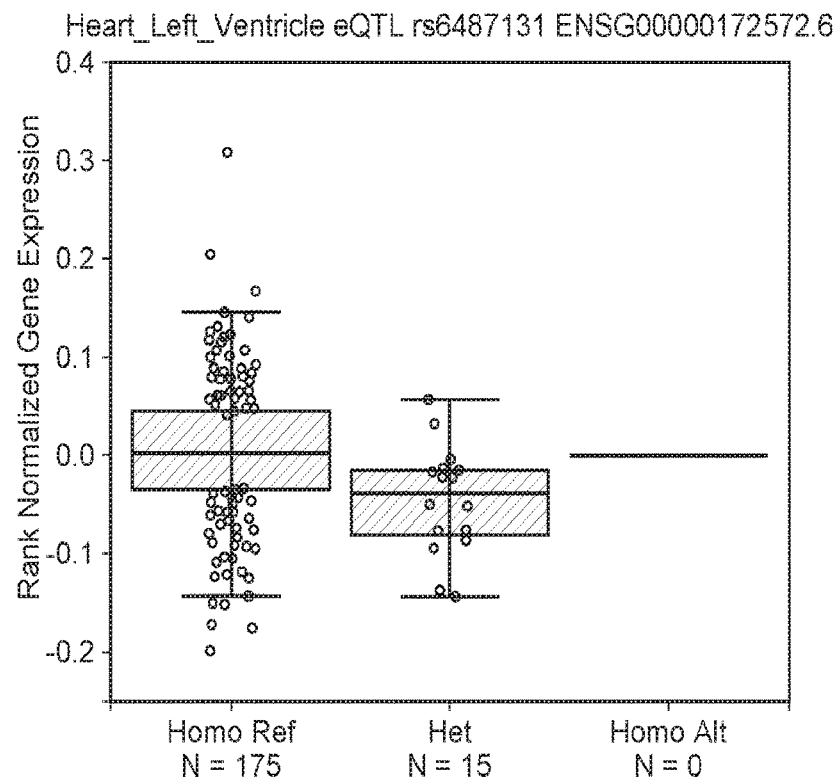

Specification includes a Sequence Listing.

rs7314545 (P = 0.000436; OR = 16.6 [92.1-129.4])

☐ 66.67% 28 C/C
▨ 33.33% 14 C/T

☐ 97.62% 41 C/C
▨ 2.38% 1 C/T rs6487132 (P = 0.000677; OR = 15.6 [2.0-122.6])

☐ 68.29% 28 A/A
▨ 31.71% 13 A/G

☐ 97.62% 41 A/A
▨ 2.38% 1 A/G rs6487131 (P = 0.000436; OR = 16.6 [92.1-129.4])

☐ 66.67% 28 C/C
▨ 33.33% 14 C/T

☐ 97.62% 41 C/C
▨ 2.38% 1 C/T

Severe                              Mild

COMPOSITIONS AND METHODS FOR PROVIDING A PROGNOSIS FOR INFLUENZA INFECTION

This application claims priority to U.S. Provisional Application No. 62/357,569, filed on Jul. 1, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is compositions and methods for providing a prognosis for a viral infection, in particular an influenza infection.

BACKGROUND

The background description includes information that may be useful in understanding the present invention. It is not an admission that any of the information provided herein is prior art or relevant to the presently claimed invention, or that any publication specifically or implicitly referenced is prior art.

Seasonal, pandemic or avian influenza viruses cause life-threatening infections [1, 2]. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Neuraminidase inhibitors are the only approved antivirals that are active against the circulating strains of influenza viruses. However, a delay in antiviral administration reduces the clinical efficacy. Furthermore, emergence of resistance to neuraminidase inhibitors has been associated with treatment failure. Human convalescent blood products have been shown to improve survival of patients with severe pandemic A (H1N1) infection, but this is not widely available.

One of the antiviral strategies is to target host cell machineries required for viral replication. The potential benefits of using host-directed antivirals include a lower likelihood for viruses to develop resistance, and a broader spectrum of antiviral activity if different viruses rely on the same mechanism for viral replication. For influenza virus, several clinically available host-directed drugs have undergone clinical trials. DAS181, a sialidase which cleaves the sialic acids of the cellular receptor for influenza virus (see United States Patent Application Publication No. 2013/0280332, to Moss et al) has been shown to decrease viral shedding but did not hasten symptom resolution in patients with influenza virus infection. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Nitazoxanide (see U.S. Pat. No. 9,023,877, to Rossignol et al.), which blocks the maturation and intracellular trafficking of viral hemagglutinin, was associated with improvement in symptoms in a double-blind randomized placebo-controlled trial. Arbidol (see U.S. patent application Ser. No. 12/159,563, to Leneva) is a lipid modulator used to treat influenza, mainly in Russia and China. Recent findings indicate that mycophenolic acid (see United States Patent Application Publication No. 2016/0052905, to Lee et al.) has antiviral activity against influenza viruses.

There are two main approaches to identify host factors as targets for antivirals. The first approach is to identify host factors that are important for viral replication. This can be achieved by using in vitro screening systems, with the importance of each gene verified by knockdown or over-expression of the candidate gene in vitro or in animal models. The second approach is to identify genetic variations that are significantly different between severe and mild cases [14]. Using the latter approach CD55, SFTPB, TMPRSS2 and LGALS1 have been identified as host susceptibility genes for the 2009 pandemic influenza A(H1N1) (A[H1N1]pdm09) or A(H7N9) virus infection (see To K K, Zhou J, Song Y Q, et al. Surfactant protein B gene polymorphism is associated with severe influenza. Chest 2014; 145:1237-43; Zhou J, To K K, Dong H, et al. A functional variation in CD55 increases the severity of 2009 pandemic H1N1 influenza A virus infection. J Infect Dis 2012; 206: 495-503; Chen Y, Zhou J, Cheng Z, et al. Functional variants regulating LGALS1 (Galectin 1) expression affect human susceptibility to influenza A(H7N9). Sci Rep 2015; 5:8517; Cheng Z, Zhou J, To K K, et al. Identification of TMPRSS2 as a Susceptibility Gene for Severe 2009 Pandemic A(H1N1) Influenza and A(H7N9) Influenza. J Infect Dis 2015; 212:1214-21). Such genetic markers, however, fail to provide prognostic guidelines to the medical practitioner.

Thus, there is still a need for novel and clinically useful compositions and methods that provide prognostic information to a medical practitioner treating influenza.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

The inventive subject matter provides apparatus, systems and methods in which the prognosis for an individual that is infected with an influenza virus can be estimated by determining the presence or absence of certain genetic mutations in that individual. Suitable genetic mutations include a PDE3A mutation, where severity of the viral infection is increased when the PDE3A mutation results in reduced PDE3A function.

One embodiment of the inventive concept is a method of providing a prognosis for an individual by testing a sample (such as such as blood, saliva, a nasal swab, and/or a cheek swab) obtained from an individual for the presence of a PDE3A mutation associated with reduced PDE3A function. The mutation can be a single nucleotide polymorphism (SNP), for example the one or more of the SNPs rs7314545, rs6487131, and/or rs6487132. The presence of such a mutation can be determined by genotyping (for example, by polynucleotide amplification) or by characterization of a gene produce (for example, by an immunochemical assay). The reduction in PDE3A can be due to reduced activity of the gene product, reduced PDE3A gene transcription, and/or reduced PDE3A gene translation.

Another embodiment of the inventive concept is a kit for providing a prognosis for an influenza infection, which includes a first primer that is at least partially complementary to a PDE3A gene or gene transcript; and instructions for use. The primer can include a non-naturally occurring base and/or a non-naturally occurring sugar-phosphate backbone analog. In some embodiments the first primer is designed to permit detection of a SNP, such as rs7314545, rs6487131, and rs6487132. In some embodiments first primer includes a polynucleotide sequence that is at least partially complementary to a region of PDE3A from which an intron has been excised. The kit can include an additional, different primer that is at least partially complementary to a PDE3A gene or gene transcript, and that is designed to act in concert with the first primer in a polynucleotide amplification reaction. Such kit can also include a probe that is at least partially complementary to PDE3A or a PDE3A amplification product, wherein the probe comprises a detectable tag.

Another embodiment of the inventive concept is a primer for providing a prognosis for influenza infection, which includes a polynucleotide sequence that is at least partially complementary to PDE3A and can include a detectable tag. The primer can include a non-naturally occurring base and/or a non-naturally occurring sugar-phosphate backbone analog. Such a primer can be designed to permit detection of a SNP, such as rs7314545, rs6487131, and/or rs6487132. In some embodiments the primer can include a polynucleotide sequence that is at least partially complementary to a region of PDE3A from which an intron has been excised.

Another embodiment of the inventive concept is a method for assessing the clinical outcome of an influenza infection, by providing an algorithm that includes a correlation between the presence of at least one PDE3A mutation and a severe outcome of influenza infection and inputting a patient's PDE3A status to the algorithm. Such an algorithm can be a multivariate analysis that incorporates one or more additional patient factors, such as patient age, patient gender, patient immune status, patient ethnicity, patient immune status, patient lifestyle factors, presence of non-infectious disease, viral genetic factors, and/or the presence of non-PDE3A genetic markers of the patient.

Another embodiment of the inventive concept is a method for treating an influenza infection, by increasing the activity of a pro-inflammatory cytokine (such as TNFα, IL-1β, IL-6, and/or IL-32) in an infected individual. The increase in activity can be accomplished by supplying the pro-inflammatory cytokine to the individual as a prodrug and/or prodrug conjugate (e.g. a polyethylene glycol conjugate). In some embodiments the activity is increased by providing a pro-inflammatory cytokine agonist. In some embodiments the activity is increased by increasing expression and/or release of a pro-inflammatory cytokine.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1: FIG. 1 depicts an allelic specific expression profile of PDE3A SNPs in human left ventricle tissue.

FIGS. 2A to 2C: FIGS. 2A to 2C show differences in genetic risk of development of severe symptoms following viral influenza infection among different populations. FIG. 2A depicts SNP frequency distribution in populations experiencing severe or mild influenza. FIG. 2B shows the proportions of Chinese and Caucasian populations having high, elevated, and typical genetic risks for developing severe illness on infection with H1N1 pdm09 influenza virus infection. Populations shown are Southern Chinese in Macau; (Macau), Southern Chinese (CHS), Beijing Chinese (CHB), European (EUR), and American (AMR). FIG. 2C shows a comparison of population genetic risk distributions of Chinese and Caucasian (upper panel), and Chinese populations from different regions (lower panel). Cumulative distributions of genetic risks of having severe illness after H1N1 pdm09 infection are plotted against population percentage. Populations are designated as in FIG. 2B.

FIGS. 3A and 3B: FIGS. 3A and 3B show the effect of viral infection on PDE3A. FIG. 3A shows increased PDE3A expression following viral infection. FIG. 3B shows increased PDE3A mRNA expression following viral infection.

FIGS. 4A and B: FIGS. 4A and 4B show the results of PDE3A siRNA knockdown studies. FIG. 4A depicts the effect of PDE3A siRNA knockdown on PDE3A expression. FIG. 4B depicts the effect of siRNA knockdown on PDE3A protein concentration.

FIGS. 5A to 5C: FIGS. 5A to 5C show the effect of siRNA on viral replication in treated cells. FIGS. 5A and 5B depict the effect of PDE3A siRNA on viral titer for various influenza strains in transfected cells at 24 hours and 48 hours post-infection, respectively. FIG. 5C shows expression of influenza virus nucleoprotein in cells transfected with PDE3A siRNA.

FIGS. 6A and 6B: FIGS. 6A and 6B show the results of PDE3B siRNA knockdown studies. FIG. 6A depicts the effect of siRNA knockdown on PDE3B expression. FIG. 6B depicts the effect of PDE3B siRNA on influenza virus titer in transfected cells.

FIGS. 7A and 7B: FIGS. 7A and 7B show the results if siRNA knockdown on cytokine expression in influenza infected cells. FIG. 7A shows typical result for IL-6 expression. FIG. 7B shows typical results for IL-32 expression.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods that permit identification of individuals with an increased risk of severe (e.g. life threatening) sequelae following infection with an influenza virus. The inventors have identified a previously unsuspected gene, PDE3A, using a 2-tier genetic association study, and have further identified single nucleotide polymorphisms (SNPs) associated with the development of severe disease, specifically rs7314545, rs6487131, and rs6487132. Such genetic markers can be used in isolation or in combination with other patient-specific factors (e.g. age, gender, immune status, co-infection, other patient genetic markers, viral genetic markers) to provide a health care professional with a prognostic tool useful in indicating effects and/or outcomes of influenza infection. A role of PDE3A in viral replication and host inflammatory response in vitro has also been identified.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The Inventors have identified and investigated the role of a host factor, PDE3A, in the outcome of influenza virus infection. PDE3A was identified and confirmed as a host factor influencing the disease severity of influenza virus (for example influenza A(H1N1)pdm09) infection based on genetic association studies comparing severe and mild influenza cases, and between severe influenza cases and the general population. Multivariate analysis confirmed that the genetic association between PDE3A SNPs rs7314545/rs6487132 and influenza infection was not due to known clinical risk factors. In addition in vitro studies showed that influenza virus infection induced the expression of PDE3A. Significantly, suppression of PDE3A expression was found to enhance viral replication of influenza A(H1N1)pdm09 virus, A(H5N1) virus, and A(H7N9) virus, and to enhance the expression of pro-inflammatory cytokine (such as IL-6 and/or IL-32) mRNA expression in influenza infected cells. Surprisingly, inventors have found that PDE3A can act as an antiviral and anti-inflammatory host factor for A(H1N1) pdm09 virus. In addition, identifiable genetic variations of PDE3A gene can predispose infected individuals to severe influenza virus infection. While not wishing to be bound by theory, the inventors believe that this may be a result of increased viral replication and cytokine response in individuals having such genetic variations.

Embodiments of the inventive concept include compositions and methods for determining that an individual has and/or is at risk of developing severe complications (e.g. illness requiring hospitalization, illness requiring respiratory support) and/or death on infection with an influenza virus.

Methods of the inventive concept can include methodologies that can identify the presence of mutations in the PDE3A gene that negatively affect expression and/or function of the gene product as predisposing an individual having such a mutation to severe complications and/or death on infection with an influenza virus. Such mutations include mutations in upstream sequences that influence transcription, translocations, substitutions of one or more nucleotides (for example, a single nucleotide polymorphisms or SNP), deletions, and insertions of a PDE3A gene, a regulatory element associated with a PDE3A gene, and/or a gene involved in regulation of a PDE3A gene. In a preferred embodiment of the inventive concept the mutation is embodied in one or more SNPs within a structural and/or functional portion and/or region of PDE3A and/or an associated regulatory region. Such mutations can be identified using statistical techniques related to sequelae of influenza infection as applied to genomic data, as described below. Identification of the presence of such a PDE3A mutation in an individual can be used prognostically as an indicator of the severity of an influenza infection, and thereby provide guidance to a healthcare provider in determining a course of treatment. Alternatively, other mutations shown to be linked to PDE3A mutations so identified can be utilized to identify an individual susceptible to severe influenza infection. Examples of suitable mutations include the SNPs designated rs7314545, rs6487131, and rs6487132.

It should be appreciated that such patient genetic markers can be used in isolation or in combination with other factors to provide a prognostic tool for influenza infection. Other factors can include patient age, patient gender, patient immune status, patient ethnicity, patient immune status, patient lifestyle factors (e.g. alcohol use, drug use, tobacco use), and/or presence of non-infectious disease (e.g. diabetes, allergy, emphysema, cancer, heart disease). In some embodiments viral genetic factors can be utilized as part of the prognostic tool or method. In still other embodiments, patient genetic markers other than those noted above can be used as part of such a prognostic tool or method. For example, such markers or factors can be utilized in a multivariate analysis that incorporates PDE3A mutations. Such a multivariate analysis form at least part of a prognostic and/or clinical decision algorithm useful to a clinician in determining a course of treatment for an individual having influenza.

Any method suitable for use in determining genetic composition can be utilized. Typically such methods can incorporate polynucleotide amplification technologies, such as PCR, reverse transcription PCR, real time PCR, and endpoint PCR. Alternatively, linear polynucleotide amplification methods can be utilized. In some embodiments the genetic composition of a patient sample can be determined directly (i.e. without amplification). Alternatively, gene products (e.g. proteins) can be identified. Such gene products can be identified by expression level, for example by quantitation relative to a reference protein. In some embodiments specific mutations of a protein gene product can be identified, for example through the use of specific monoclonal antibodies, protein/peptide sequence analysis, production of characteristic fragmentation products on proteolysis, etc.

Such methods can be performed manually, using an automated instrument, or in a semi-automated manner. Such methods can provide quantitative, semi-quantitative, or non-quantitative results (e.g. utilizing suitable signal or quantitative cutoff values). In some embodiments the method can be performed in a multiplex fashion (for example using individual indicator fluorophores with non-overlapping emission spectra, a printed microarray, a fluid bead array, or other means of encoding individual results), which permits characterization of two or more mutations from a single sample simultaneously. In other embodiments results are obtained in a single-plex (e.g. monoplex) manner. Alternatively, in some embodiments PDE3A mutations can be identified using an immunological method. For example, specific antibodies can be used to identify the presence of specific mutations using immunoassay techniques (for example immunofluorescence, enzyme immunoassay, or flow immunoassays). In still other embodiments an immunoassay can utilize capture of PDE3A from a sample using a specific antibody and subsequent characterization of the capture protein, for example by an activity assay and/or mass spectrometry.

Genetic tests can utilize polynucleotide primers and probes designed to hybridize to all or part of the PDE3A gene, regulatory region, or regulatory factor. Such primers and probes can include various tags or detection moieties, such as fluorescent dyes, radioactive tags, mass tags, quenching groups, haptenic groups, and so on. Such primers and/or probes can include non-naturally occurring bases and/or sugar-phosphate backbone components in order to optimize binding energy and/or stability. In some embodiments such primers and/or probes can include deliberate base mismatches, which can improve specificity. In some embodiments a primer and/or probe sequence can be complementary to a PDE3A sequence from which one or more introns has(have) been excised.

Compositions and methods of the inventive concept can be applied to any suitable patient sample. Suitable samples include body fluids such as blood, saliva, urine, mucus, and other body fluids. Suitable sample can also include tissue samples, such as cheek swabs, skin scrapings, shed epithelial cells, hair follicles, samples obtained by lavage and/or tissue biopsy, and slides obtained for histological studies.

Inventors have identified certain PDE3A SNPs (as detailed below) that are negatively associated with PDE3A expression, and are particularly useful in this regard. For example, rs6487131 is located within the predicted binding site of transcription factors CTCF, Rad21 and USF1. The genetic variations in such a transcription factor binding sites can affect the transcription activity of PDE3A. In addition, according to Genotype-Tissue Expression (GTEx) Portal (version V6)™, SNP rs6487131-TT/CT, which has high linkage with rs6487132 and rs7314545, is significantly associated with a lower expression of PDE3A in the left ventricle of the heart (P=0.017), where PDE3A is expressed most abundantly [33] (see FIG. 1).

Without wishing to be bound by theory, Inventors believe that individuals with such (or similarly associated) alleles can have a lower level of PDE3A expression and/or lowered PDE3A induction upon influenza virus infection. Such individuals can, as a result, have an impaired capacity for viral clearance, higher viral replication and a cellular response that includes elevated proinflammatory cytokine expression (such as IL-6 and/or IL-32) as a cellular offset. Such high levels of viral replication and higher proinflammatory cytokine response are, in turn, at least partially responsible for severe influenza infection.

Surprisingly, the Inventors have found increased expression of IL-6 and IL-32 in A(H1N1)pdm09 infected cells having reduced PDE3A expression (for example, due to knockdown treatment with appropriate siRNA) when compared with control cells (for example, cells transfected with control siRNA). It should be appreciated that such findings run counter to conventional teaching, as in vitro studies have indicated that PDE3 inhibitors reduce LPS-induced cytokine production, reduce lung injury, and confer protection from endotoxin shock. Without wishing to be bound by theory, the inventors believe that PDE3A may also play a role in inflammation during influenza virus infection in humans and that such an inflammatory process can be impacted by the presence of particular PDE3A mutations.

The Inventors have shown that PDE3A can act as an antiviral host factor in influenza infection and diseases (mutations in which can lead to severe disease on infection with influenza). Inventors also believe that PDE3A can also affect disease severity via other physiological functions. For example, known physiological functions of PDE3A include the regulation of vascular smooth muscle contraction and relaxation in the heart, insulin secretion, lipolysis, oocyte maturation, and platelet aggregation.

As shown below the Inventors have found that knockdown of PDE3A (for example, via transfection with siRNA) enhances the viral replication of influenza strains A(H1N1), A(H5N1) and A(H7N9). It should be appreciated that this effect was not found in infection with influenza strain A(H3N2). The interplay between specific host and viral factors is likely to be much more complicated than a simple pathway. However, the Inventors have discovered that a strong link exists between the host factor PDE3A and at least influenza A(H1N1) (and very likely at least strains A(H5N1) and A(H7N9)). The Inventors believe that PDE3A genetic variants can, therefore, serve as useful genetic markers for prognosis of influenza, and speculate that other SNPs that are useful in this regard can be identified in other various human ethnic and/or geographic groups using the methods described below.

Another embodiment of the inventive concept is a method of treating influenza, in particular severe influenza. Such a method can include treating a patient with pro-inflammatory cytokines and/or inducing a patient to express pro-inflammatory cytokines. Suitable pro-inflammatory cytokines include TNFα, IL-1β, IL-6, and IL-32. Such pro-inflammatory cytokines can be supplied as prodrugs and/or in modified form. For example, suitable pro-inflammatory cytokines can be provided as conjugates (for example, polyethylene glycol conjugates). Alternatively, an individual with influenza can be treated with compounds that increase production and/or release of pro-inflammatory cytokines.

Another embodiment of the inventive concept is a method of treating influenza by modulating the expression of PDE3A and/or the use of PDE3A agonists. For example, in a method of the inventive concept a person with influenza can be treated using a PDE3A-inducing compound. Alternatively, in other embodiments a person with influenza can be treated with a compound that acts as a PDE3A agonist to provide an effect similar to that of increased PDE3A production and/or release. It is contemplated that such induction can provide levels of PDE3A activity that are at least equivalent to that of a normal individual in a person with a PDE3A mutation that affects expression and/or activity of PDE3A gene product. In some embodiments such therapy can provide PDE3A activity that exceeds that of a normal individual by 10%, 50%, 100% or more in normal individuals and/or individuals carrying PDE3A mutations that impact expression and/or activity of the PDE3A gene product.

Methods

Patients: This study consisted of Chinese adult patients diagnosed with A(H1N1)pdm09 infection between May 2009 and January 2012 in Hong Kong. The first patient cohort consisted of 42 severe and 42 mild cases matched for gender, age and number of underlying risk conditions. A second cohort of patients consisted of 122 severe cases and 197 mild cases who had successful genotyping of at least one of the following PDE3A gene single nucleotide polymorphisms (SNPs): rs7314545, rs6487131 or rs6487132. Patients were considered to have severe disease if they required oxygen supplementation, admitted to the intensive care unit, or died. Exclusion criteria include non-Chinese ethnicity, age <18 years, archived specimens not sufficient for genotyping, or the essential clinical information could not be retrieved from the clinical management system.

Genotyping of patients with A(H1N1)pdm09 infection: The first cohort of patients was genotyped using Genome-Wide Human SNP Array 6.0™ (Affymetrix Inc.). The SNPs rs7314545, rs6487131 and rs6487132 were genotyped using the MassARRAY System™ (Sequenom Inc.). Genomic DNA for genotyping was obtained from archived blood specimens or respiratory tract specimens.

Genotype data for the general population of Han Chinese: Subjects were recruited with written informed consent from the University Hospital, Macau University of Science and Technology (MUST), Macau between 2014 and 2015. Only Chinese subjects were included. All samples were genotyped using Human Omni ZhongHua-8 BeadChips™ (Illumina) following the manufacturer's instructions. The SNPs included rs6487132 and rs6487131. However, rs7314545 was not included in the chip. Additional genotype data for Han Chinese were also extracted from the data of Han Chinese in Beijing (CHB) and Southern Han Chinese (CHS) in the 1000 Genomes Project Phase 3.

Viruses and cell lines: All virus strains used in this study were clinical strains, and included influenza virus subtypes A(H1N1)pdm09 (A/Hong Kong/415742/2009 [H1N1-2009] and A/Hong Kong/402467/2014 [H1N1-2014]), A(H3N2) (A/Hong Kong/447572/2011 [H3N2-2011]), A(H5N1) (A/Vietnam/1194/2004 [H5N1-2004]) and A(H7N9) (A/Anhui/1/2013 [H7N9-2013-AH1] and A/Zhejiang/DTID-ZJU01/2013 [H7N9-2013-ZJ1]) [12, 21]. These viruses were propagated in Madin Darby canine kidney (mdck) cells. Human alveolar epithelial cell line A549 and human bronchial epithelial cell line Calu-3 were used for in vitro experiments.

Determination of PDE3A mRNA expression in A549 and Calu-3 cells infected with A(H1N1)pdm09 virus: A549 cells were seeded onto 96-well plates with Dulbecco's Modified Eagle's medium (DMEM) supplemented with 10% fetal bovine serum (FBS), 0.025 M of HEPES buffer, 100 units/ml of penicillin G, 100 m/ml of Streptomycin, 20 m/ml of gentamicin and 20 units/ml of nystatin (all reagents from Thermo Fisher Scientific, MA, USA). The culture plates were incubated at 37° C. and 5% $CO_2$. When cells reached 100% confluency, the cells were washed, and were inoculated with H1N1-2009 as added at a multiplicity of infection (MOI) of 1 with DMEM, 3% bovine serum albumin (Sigma-Aldrich, MO, United States) and 1 m/ml L-1-tosylamide-2-phenylethyl chloromethyl ketone (TPCK)-treated trypsin (Sigma-Aldrich). For controls, DMEM was added instead of the virus. At indicated time points post-infection, PDE3A mRNA expression in cell lysate was determined using reverse transcription-quantitative polymerase chain reaction (RT-qPCR) as described previously with modifications [22]. Briefly, RNA was extracted from cell lysates using the RNeasy Mini Kit™ (Qiagen, Hilden, Germany). Extracted RNA was treated with DNase I (Thermo Fisher Scientific). Reverse transcription was performed using the PrimeScript RT Master Mix (Perfect Real Time) Kit™ (Takara Bio, China) according to manufacturer's instruction. cDNA was amplified in a LightCycler™ 2.0 (Roche, Upper Bavaria, Germany) using specific primers as listed in Table 1 [23]. The 20 μl PCR reaction mixture contained 2 μl cDNA, 2 μl FastStart DNA Master SYBR Green I Mix™, 0.5 μM of forward and reverse primers, nuclease-free $H_2O$ and $MgCl_2$. Melting curve analysis was performed to validate the product identity. Glyceraldehyde-3-phosphate dehydrogenase (GAPDH) mRNA expression was used as a reference gene for normalization.

TABLE 1

| Primer name | Primer sequence |
|---|---|
| PDE3A-Forward (SEQ ID NO. 1) | 5'-GATGATAAATACGGATGTCTGTC-3' |
| PDE3A-Reverse (SEQ ID NO. 2) | 5'-ACCGCCTGAGGAGCACTAG-3' |
| PDE3B-Forward (SEQ ID NO. 3) | 5'-AAAGGGGATAGAAAACTTAACAAGG-3' |
| PDE3B-Reverse (SEQ ID NO. 4) | 5'-CAGGTAGCAATCCTGAAGTTCC-3' |
| PDE4A-Forward (SEQ ID NO. 5) | 5'-TTCACGGACCTGGAGATTC-3' |
| PDE4A-Reverse (SEQ ID NO. 6) | 5'-TGAGGAACTGGTTGGAGAC-3' |
| PDE4B-Forward (SEQ ID NO. 7) | 5'-CAAGCCTAAACAATACAAGCATC-3' |
| PDE4B-Reverse (SEQ ID NO. 8) | 5'-TGAGAATATCCAGCCACATTAAAG-3' |
| PDE4C-Forward (SEQ ID NO. 9) | 5'-CACCTGGCTGTGGGCTTC-3' |
| PDE4C-Reverse (SEQ ID NO. 10) | 5'-ACTCAGTCGCTGCTTGGC-3' |
| PDE4D-Forward (SEQ ID NO. 11) | 5'-CTACTGGCTGATTTGAAGACTATG-3' |
| PDE4D-Reverse (SEQ ID NO. 12) | 5'-GCTGGAGAGGCTTTGTTGG-3' |
| PDE8A-Forward (SEQ ID NO. 13) | 5'-ATGTTTGCTCGCTTTGGAATC-3' |
| PDE8A-Reverse (SEQ ID NO. 14) | 5'-CAGAATGTGTAGAATTGTGGTAGG-3' |
| GAPDH-Forward (SEQ ID NO. 15) | 5'-ATTCCACCCATGGCAAATTC-3' |
| GAPDH-reverse (SEQ ID NO. 16) | 5'-CGCTCCTGGAAGATGGTGAT-3' |
| IL-6-Forward (SEQ ID NO. 17) | 5'-GGCTGCAGGACATGACAACT-3' |
| IL-6-Reverse (SEQ ID NO. 18) | 5'-ATCTGAGGTGCCCATGCTAC-3' |
| IL-32-Forward (SEQ ID NO. 19) | 5'-AATCAGGACGTGGACAGGTGATGT-3' |
| IL-32-Reverse (SEQ ID NO. 20) | 5'-TGCTCCTCATAATAAGCCGCCACT-3' |
| TNF-α-Forward (SEQ ID NO. 21) | 5'-CAAGGACAGCAGAGGACCAG-3' |
| TNF-α-Reverse (SEQ ID NO. 22) | 5'-TGGCGTCTGAGGGTTGTTTT-3' |

TABLE 1-continued

| Primer name | Primer sequence |
|---|---|
| IP-10-Forward (SEQ ID NO. 23) | 5'-AGCAGAGGAACCTCCAGTCT-3' |
| IP-10-Reverse (SEQ ID NO. 24) | 5'-ATGCAGGTACAGCGTACAGT-3' |
| IFN-β-Forward (SEQ ID NO. 25) | 5'-GCCGCATTGACCATCT-3' |
| IFN-β-Reverse (SEQ ID NO. 26) | 5'-CACAGTGACTGTACTCCT-3' |

For Calu-3 cells, the conditions were the same as for A549 cells except that the culture medium before infection contains DMEM/Nutrient Mixture F-12 (DMEM/F12) instead of DMEM, and Calu3 cells were inoculated with the A(H1N1)pdm09 virus with 0.5 μg/ml TPCK-treated trypsin instead of 1 μg/ml.

Knockdown of PDE3A or PDE3B genes using small interfering RNA (siRNA) in A549 cells: A549 cells were transfected with siRNA targeting PDE3A gene (PDE3A siRNA) (siRNA ID S10184, Thermo Fisher Scientific, MA, USA), PDE3B gene (PDE3B siRNA))(siRNA ID S10188, Thermo Fisher Scientific, MA, USA) or non-targeting control siRNA (Silencer™ Select Negative Control No. 2 siRNA, Thermo Fisher Scientific, MA, USA). Briefly, 1.8× $10^5$ A549 cells per well were seeded onto 24-well tissue culture test plates (TPP™, Switzerland) and incubated in 37° C. with 5% $CO_2$. When 70%-80% cell confluency was achieved, the cells were transfected with PDE3A siRNA, PDE3B siRNA or non-targeting control siRNA using Lipofectamine™ RNAiMAX transfection reagent (Thermo Fisher Scientific, MA, USA) according to manufacturer's instructions. The knockdown efficiency was determined by comparing the PDE3A mRNA and protein expression of PDE3A-siRNA transfected cells and those of control-siRNA transfected cells. PDE3A mRNA expression was determined using RT-qPCR as described above. PDE3A protein expression was determined using Western blot as we described previously with modifications [12]. Rabbit anti-PDE3A antibody (Abcam, United Kingdom) was used as the primary antibody.

Multicycle growth assay in A549 cells: A549 cells transfected with PDE3A siRNA or non-targeting control siRNA were inoculated with different influenza virus strains at an MOI of 0.01. Viral titer in the culture supernatant at predetermined time points post-infection was determined by plaque assay as we described previously [12].

Influenza A nucleoprotein expression of A549 infected with H1N1-2009: A549 cells transfected with PDE3A siRNA or non-targeting control siRNA were inoculated with influenza virus strain H1N1-2009 at an MOI of 10. Influenza A nucleoprotein expression was determined by Western blotting analysis.

Determination of the levels of cytokines and chemokines mRNA expression: The mRNA expression of cytokines and chemokines were determined using RT-qPCR as described previously [22]. RNA extraction and RT-qPCR were performed as described for PDE3A mRNA expression, except that specific primers for the cytokines and chemokines were used (see Table 1).

Statistical analysis: IBM SPSS Statistics version 21™ was employed for statistical analysis unless otherwise specified. The Fisher's exact test and Mann-Whitney U test were used for the comparison of categorical variables and continuous variables, respectively. Genetic association was analyzed using PLINK version 1.9™. Multivariate analysis was performed using backward stepwise multivariate regression analysis. A p-value of <0.05 was considered statistically significant.

Typical Results

PDE3A gene variants were significantly associated with disease severity. The first cohort of 84 patients consisted of 42 severe and 42 mild cases of A(H1N1)pdm09 infection who were matched for age, gender and underlying conditions, and the SNPs of these severe and mild cases were compared. The comparison of the demographics and underlying risk conditions between severe and mild cases in this first cohort has been described previously [15]. Although none of the SNPs reached the cutoff for genome-wide significant result of $P<5\times10^{-8}$, the PDE3A gene SNPs rs7314545, rs6487131, and rs6487132 had odds ratio >15 and allelic association with P<0.001 (see FIG. 2).

When comparing the allele frequencies of these 3 SNPs between the severe cases in this first cohort and the general Han Chinese population, the odds ratio ranged from 3.38-3.96, with allelic association P values between $10^{-6}$ to $10^{-5}$ (see Table 2). The SNPs rs6487131 and rs6487132 were in complete linkage based on available data in the general Han Chinese population. The SNP rs7314545 was also highly linked to rs6487131/rs6487132. One hundred and two other SNPs related to PDE3A were also screened but the P values were all above 0.001 when comparing between severe and mild cases (see Table 3).

TABLE 2

| | | Severe cases | | General Han Chinese population | | | Allelic P value (odds ratio [95% confidence interval]) | |
|---|---|---|---|---|---|---|---|---|
| | | $1^{st}$ cohort[a] (n = 42) | $2^{nd}$ cohort (n = 267) | Southern Han Chinese population in Macau[b] | CHB and CHS in 1000 genomes | Total (n = 1127) | | |
| Allele | | (A) | (B) | (n = 919) | (n = 208) | (C) | A vs C | B vs C |
| | | | | rs7314545 | | | | |
| T | | 14 (16.7) | 17 (9.7) | N/A | 20 (4.8) | 20 (4.8) | $8.21 \times 10^{-5}$ (3.96 [1.91-8.21]) | 0.026 (2.12 [1.08-4.14]) |
| C | | 70 (83.3) | 159 (90.3) | N/A | 396 (95.2) | 396 (95.2) | | |

TABLE 2-continued

| | Severe cases | | General Han Chinese population | | | Allelic P value (odds ratio [95% confidence interval]) | |
|---|---|---|---|---|---|---|---|
| | 1st cohort[a] (n = 42) | 2nd cohort (n = 267) | Southern Han Chinese population in Macau[b] | CHB and CHS in 1000 genomes | Total (n = 1127) | | |
| Allele | (A) | (B) | (n = 919) | (n = 208) | (C) | A vs C | B vs C |
| | | | rs6487132 | | | | |
| G | 13 (15.9) | 16 (9.1) | 98 (5.3) | 21 (5.1) | 119 (5.3) | $4.63 \times 10^{-5}$ (3.38 [1.82-6.29]) | 0.034 (1.79 [1.04-3.10]) |
| A | 69 (84.2) | 160 (90.9) | 1740 (94.7) | 395 (95.0) | 2135 (94.7) | | |
| | | | rs6487131 | | | | |
| T | 14 (16.7) | 12 (7.2) | 97 (5.3) | 21 (5.1) | 118 (5.2) | $8.451 \times 10^{-6}$ (3.62 [1.97-6.61]) | 0.2728 (1.41 [0.76-2.61]) |
| C | 70 (83.3) | 154 (92.8) | 1739 (94.7) | 395 (95.0) | 2134 (94.8) | | |

TABLE 3

| dbSNP rs# | P value | dbSNP rs# | P value | dbSNP rs# | P value |
|---|---|---|---|---|---|
| rs10047560 | 1 | rs11045331 | 1 | rs4762965 | 0.03299 |
| rs10734706 | 1 | rs11045332 | 1 | rs4762967 | 1 |
| rs10743369 | 1 | rs11045335 | 1 | rs4762971 | 1 |
| rs10743378 | 1 | rs11045355 | 1 | rs4762975 | 1 |
| rs10743383 | 1 | rs11045356 | 1 | rs4762978 | 1 |
| rs10770650 | 1 | rs11045357 | 1 | rs5014033 | 1 |
| rs10770652 | 1 | rs11045359 | 1 | rs5014035 | 1 |
| rs10770658 | 1 | rs11833395 | 1 | rs6487083 | 1 |
| rs10770665 | 1 | rs12311494 | 1 | rs6487091 | 1 |
| rs10770681 | 1 | rs12311612 | 1 | rs6487097 | 1 |
| rs10770687 | 1 | rs12314390 | 1 | rs6487098 | 1 |
| rs10841501 | 1 | rs12426222 | 1 | rs6487101 | 1 |
| rs10841506 | 1 | rs12580173 | 1 | rs7134150 | 1 |
| rs10841522 | 1 | rs12829557 | 1 | rs7134968 | 1 |
| rs10841527 | 1 | rs12832108 | 1 | rs7136256 | 1 |
| rs10841528 | 1 | rs1348581 | 1 | rs7295612 | 1 |
| rs10841543 | 1 | rs1444628 | 1 | rs7302500 | 1 |
| rs10841549 | 1 | rs1444646 | 1 | rs7304649 | 1 |
| rs10841588 | 0.007053 | rs1515775 | 1 | rs7304868 | 1 |
| rs11045205 | 1 | rs1822755 | 1 | rs7305532 | 1 |
| rs11045232 | 1 | rs3919734 | 1 | rs7316566 | 1 |
| rs11045234 | 1 | rs4304839 | 1 | rs7488869 | 1 |
| rs11045249 | 1 | rs4326884 | 1 | rs7489210 | 1 |
| rs11045256 | 1 | rs4340100 | 1 | rs7959560 | 1 |
| rs11045265 | 1 | rs4359258 | 1 | rs7961297 | 1 |
| rs11045271 | 1 | rs4393371 | 1 | rs7961678 | 1 |
| rs11045272 | 1 | rs4430560 | 1 | rs7967522 | 1 |
| rs11045279 | 1 | rs4499055 | 1 | rs7971334 | 1 |
| rs11045299 | 1 | rs4502032 | 1 | rs7974916 | 1 |
| rs11045301 | 1 | rs4609649 | 1 | rs7977226 | 1 |
| rs11045313 | 1 | rs4614506 | 1 | rs7977337 | 1 |
| rs11045316 | 1 | rs4762758 | 1 | rs7977362 | 1 |
| rs11045322 | 1 | rs4762759 | 1 | rs9669439 | 1 |
| rs11045323 | 1 | rs4762950 | 1 | rs9971816 | 1 |

Figure 2B:
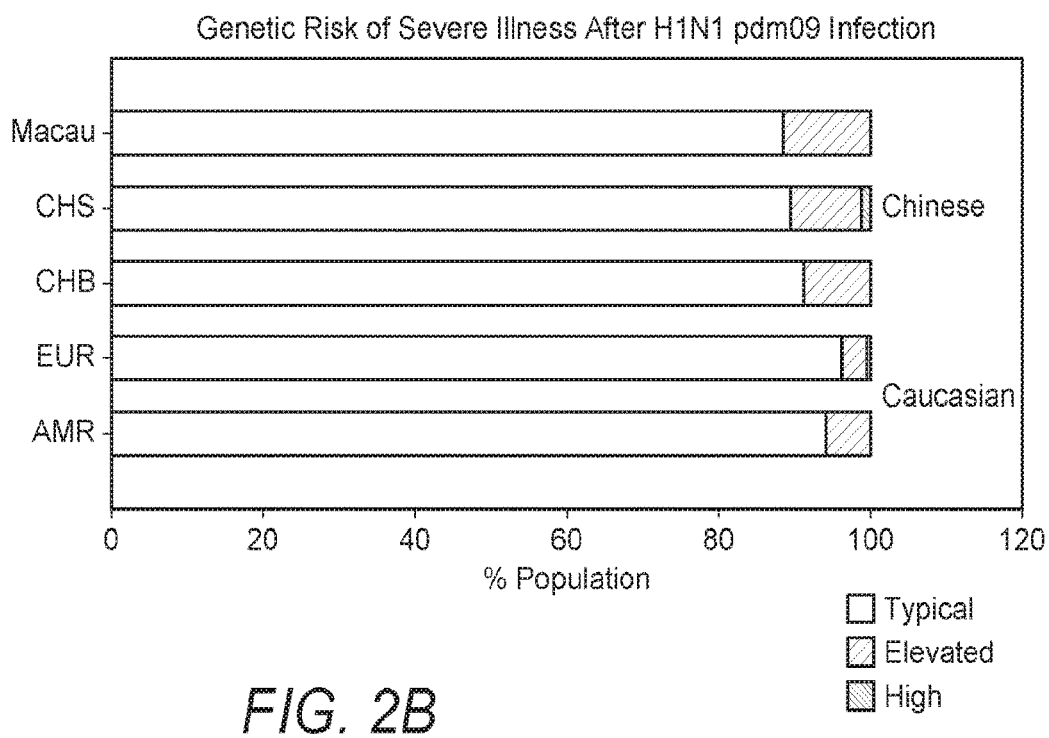
Figure 2A:
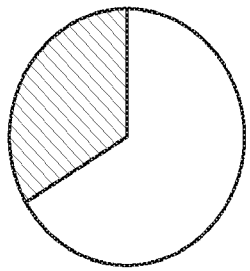
Figure 2A:
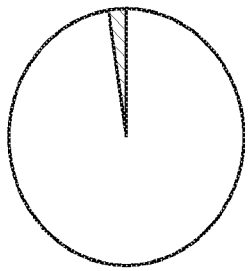
Figure 2A:
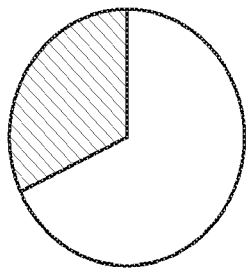
Figure 2A:
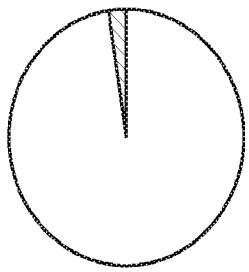
Figure 2A:
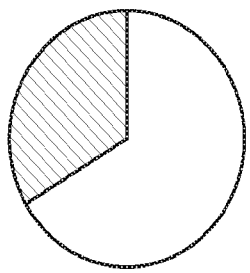
Figure 2A:
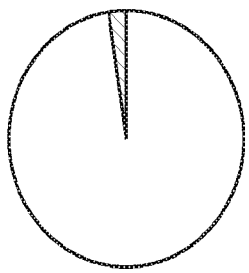
Figure 2C:
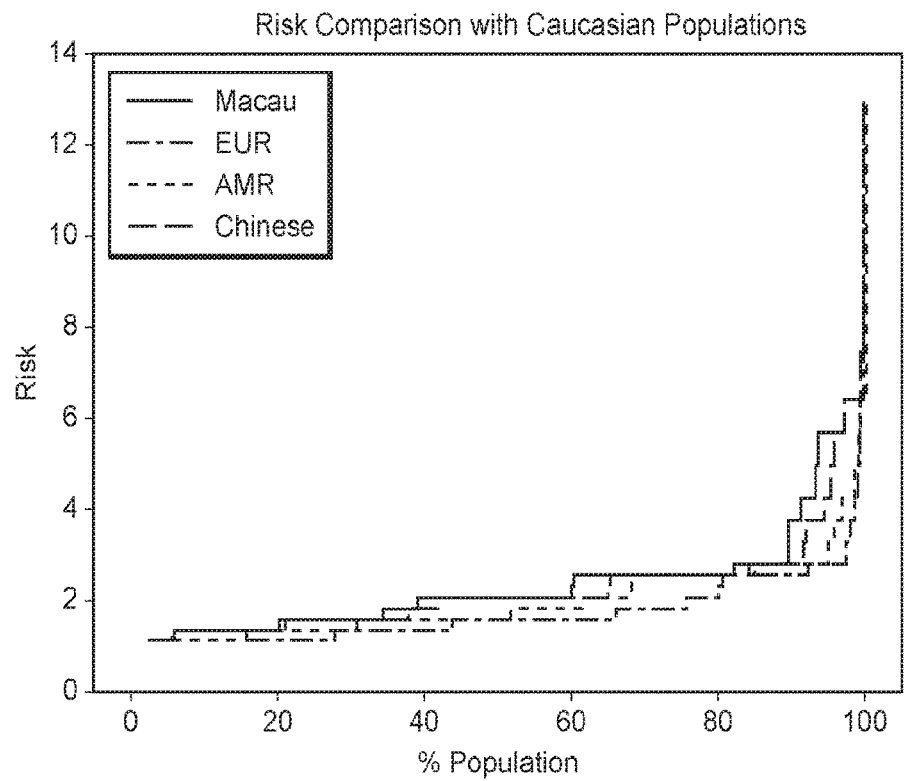
Figure 2C:
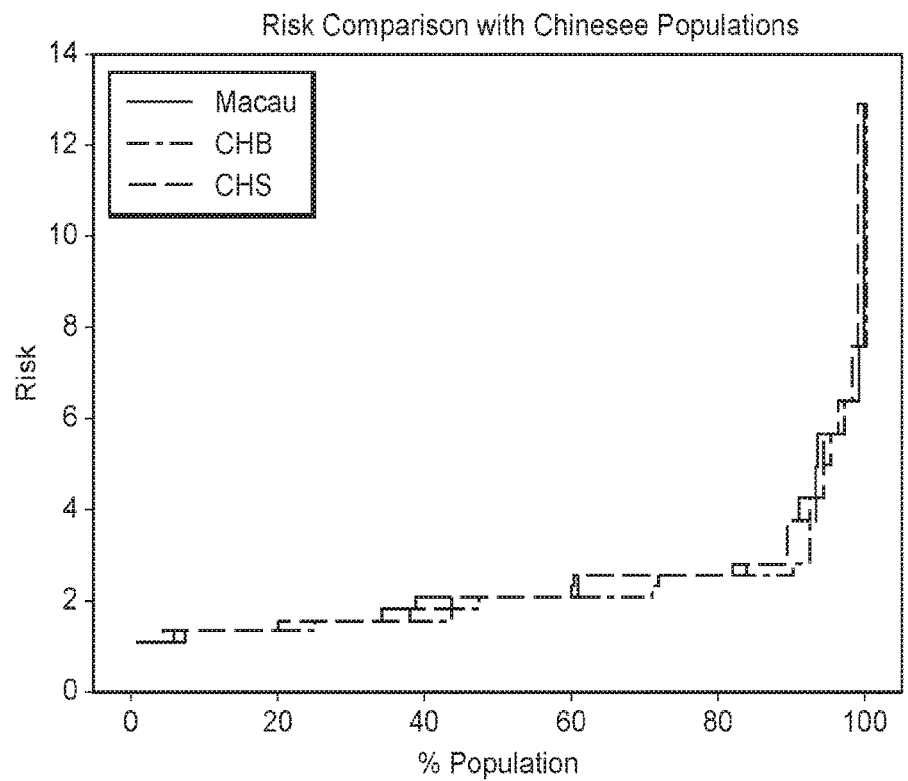

The Inventors have found that mutations (such as SNPs) of the PDE3A gene can be used to predict whether an individual is likely to develop severe illness after influenza infection. For example, by detecting the risk-associated T-allele of rs6487131, 0.2%, 11.1% and 88.5% of Southern Chinese population in Macau would be expected to have high, elevated, and typical genetic risks of having severe symptoms on H1N1 pdm09 infection, respectively (see FIG. 2B). The genetic risk appears to be higher in Macau than in other Chinese populations, as well as Western populations. FIG. 2C shows a comparison of population genetic risks among Chinese and Caucasian populations using the genetic markers rs6487131, rs2070788 and rs1130866 of the PDE3A gene. The Southern Chinese population in Macau showed a significantly higher genetic risk of having severe syndromes after H1N1 pdm09 infection when compared with American and European populations (P<0.001, Kruskal-Wallis test; P<0.001, Dunn's pairwise comparison) (see FIG. 2C, upper panel). On the other hand, no significant difference was found among Southern Chinese and Beijing Chinese in 1000 Genomes Projects, and Southern Chinese in Macau (P=0.067, Kruskal-Wallis test) (see FIG. 2C, lower panel).

PDE3A is a cyclic nucleotide phosphodiesterase which regulates the intracellular levels of the cellular second messenger cyclic adenosine monophosphate (cAMP) and cyclic guanosine monophosphate (cGMP). There is no previously known association between PDE3A and pathogenesis of viral infections.

To confirm the genetic association between PDE3A SNP and the disease severity of A(H1N1)pdm09 infection, the distributions of rs7314545, rs6487131, and rs6487132 were characterized in a second independent cohort of 324 patients with A(H1N1)pdm09 infection. At least one of these SNPs was successfully genotyped in 319 patients (98.5%), consisting of 122 severe and 197 mild cases. The alleles rs7314545-T (P=0.068) and rs6487132-G (P=0.068) were over-represented among patients with severe A(H1N1) pdm09 infection when compared to patients with mild disease, almost reaching statistical significance (see Table 4).

TABLE 4

| | Disease severity | | |
|---|---|---|---|
| | Severe[a] (n = 122) | Mild[a] (n = 197) | P |
| Demographics | | | |
| Age, median years (interquartile range) | 57 (49.75-66.5) | 37 (23.0-54.0) | <0.001 |
| Female | 46 (37.7) | 116 (58.9) | <0.001 |
| Risk conditions | | | |
| Age ≥65 years | 34 (27.9) | 26 (13.2) | 0.002 |
| Pregnant women | 1 (0.8) | 7 (3.6) | 0.161 |
| Chronic pulmonary disease | 47 (38.5) | 20 (10.2) | <0.001 |
| Chronic cardiac disease | 33 (27.0) | 19 (9.6) | <0.001 |
| Metabolic disorders | 40 (32.8) | 29 (14.7) | <0.001 |
| Chronic renal disease | 16 (13.1) | 10 (5.1) | 0.019 |
| Chronic hepatic disease | 3 (2.5) | 5 (2.5) | 1.000 |
| Neurological conditions | 20 (16.4) | 10 (5.1) | 0.001 |
| Hemoglobinopathies | 1 (0.8) | 2 (1.0) | 1.000 |
| Immunosuppression | 18 (14.8) | 34 (17.3) | 0.641 |
| Obesity | 23 (18.9) | 0 (0) | <0.001 |
| Genotype distribution | | | |
| rs7314545[a] | TT: 2 (1.7%) | TT: 0 (0%) | 0.068[d] |
| | TC: 16 (13.2%) | TC: 18 (9.4%) | |
| | CC: 103 (85.1%) | CC: 174 (90.6%) | |
| | T: 20 (8.3%) | T: 18 (4.7%) | |
| | C: 222 (91.7%) | C: 366 (95.3%) | |
| rs6487132[b] | GG: 2 (1.7%) | GG: 0 (0%) | 0.068[d] |
| | GA: 14 (11.6%) | GA: 16 (8.2%) | |
| | AA: 105 (86.8%) | AA: 180 (91.8%) | |
| | G: 18 (7.4%) | G: 16 (4.1%) | |
| | A: 224 (92.6%) | A: 376 (95.9%) | |
| rs6487131[c] | TT: 2 (1.8%) | TT: 0 (0%) | 0.260[d] |
| | TC: 9 (7.9%) | TC: 14 (7.5%) | |
| | CC: 103 (90.4%) | CC: 173 (92.5%) | |
| | T: 13 (5.7%) | T: 14 (3.7%) | |
| | C: 215 (94.3%) | C: 360 (96.3%) | |

Since the level of PDE3A has been shown to be down-regulated in patients with dilated cardiomyopathy or ischemic heart disease, data from this second cohort was re-analyzed while limiting data to subjects without evidence of chronic heart disease in order to eliminate the effect of this confounding factor (see Table 5).

TABLE 5

| | Disease severity | | |
|---|---|---|---|
| | Severe[a] (n = 89) | Mild[a] (n = 178) | P |
| Demographics | | | |
| Age, median years (interquartile range) | 56.0 (45.0-62.0) | 34.0 (23.0-50.0) | <0.001 |
| Female | 33 (37.1) | 107 (60.1) | <0.001 |
| Risk conditions | | | |
| Age ≥65 years | 15 (16.9) | 14 (7.9) | 0.036 |
| Pregnant women | 1 (1.1) | 7 (3.9) | 0.276 |
| Chronic pulmonary disease | 33 (37.1) | 16 (9.0) | <0.001 |
| Metabolic disorders | 23 (25.8) | 17 (9.6) | 0.001 |
| Chronic renal disease | 8 (9.0) | 6 (3.2) | 0.077 |
| Chronic hepatic disease | 1 (1.1) | 3 (1.7) | 1.000 |
| Neurological conditions | 8 (9.0) | 7 (3.9) | 0.099 |
| Hemoglobinopathies | 0 (0) | 2 (1.1) | 0.554 |
| Immunosuppression | 13 (14.6) | 28 (15.7) | 0.859 |
| Obesity | 19 (21.3) | 0 (0) | <0.001 |

The alleles rs7314545-T (9.70% vs 4.1%, P=0.010), rs6487132-G (9.1% vs 3.4%, P=0.006) and rs6487131-T (7.2% vs 3.0%, P=0.029) were significantly over-represented in patients with severe A(H1N1)pdm09 infection when compared to those with mild disease with the elimination of the cardiac factor. The alleles rs7314545-T (9.7% vs 4.8%, P=0.026) and rs6487132-G (9.1% vs 5.3%, P=0.034) were also significantly over-represented in patients with severe A(H1N1)pdm09 infection when comparing with the general Han Chinese population (see Table 2). Using the dominant model, univariate analysis showed that the genotypes rs7314545-TT/CT (17.0% vs 8.1%, P=0.030) and rs6487132-GG/AG (15.9% vs 6.8%, P=0.019) were significantly over-represented in patients with severe disease when compared to mild disease. In the multivariate analysis, both rs7314545-TT/CT (P=0.006) and rs6487132-GG/AG (P=0.009) were confirmed to be independent risk factors for severe A(H1N1)pdm09 infection. Note that rs7314545-TT/CT and rs6487132-GG/AG were analyzed separately in the multivariate analysis because these were highly linked.

Figure 3A:
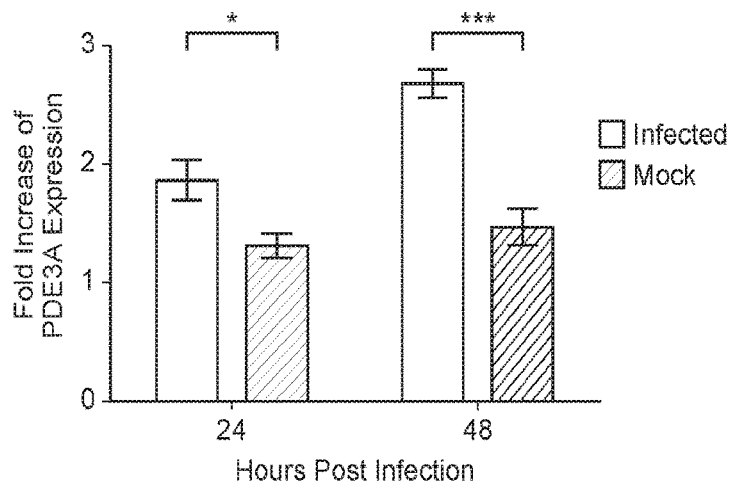
Figure 3B:
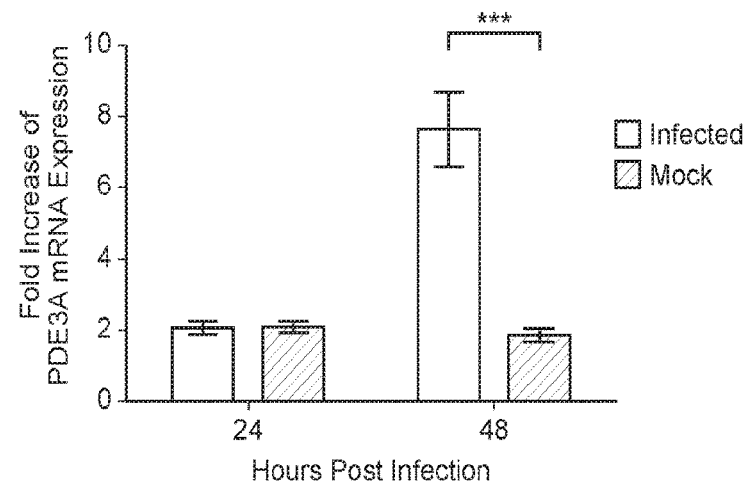

A(H1N1)pdm09 virus infection upregulated PDE3A mRNA expression in human lung epithelial cell lines: To determine the effect of A(H1N1)pdm09 virus infection on PDE3A mRNA expression, alveolar epithelial cell A549 and bronchial epithelial cell Calu-3 were infected with H1N1-2009, and expression of PDE3A mRNA in the cell lysates was determined. PDE3A mRNA expression was significantly higher in H1N1-2009-infected A549 and Calu-3 cells than those of non-infected cells (see FIG. 3). Hence, H1N1-2009 infection induces PDE3A expression in human airway epithelial cells.

PDE3A knockdown enhanced viral replication of A(H1N1)pdm09, A(H5N1), A(H7N9), but reduced viral replication for A(H3N2) virus: To determine whether PDE3A affects influenza virus infection, virus replication between A549 cells with knockdown of PDE3A using PDE3A-specific siRNA was compared with A549 cells transfected with control siRNA. PDE3A knockdown was confirmed by both RT-qPCR and by Western Blot analysis (see FIG. 4).

PDE3A siRNA used in our experiments did not significantly affect the expression of other phosphodiesterases tested, specifically PDE3B, PDE4A, PDE4B, PDE4D and PDE8A (see Table 6).

TABLE 6

| Gene | Inhibition of mRNA expression in PDE3A knockdown A549 cells relative to control. Mean ± SEM |
| --- | --- |
| PDE3A | 85.3% ± 2.1% |
| PDE3B | −4.1% ± 16.5% |
| PDE4A | 6.9% ± 2.3% |
| PDE4B | −11.0% ± 13.8% |
| PDE4C | mRNA not detected |
| PDE4D | −13.8% ± 24.8% |
| PDE8A | 3.4% ± 20.8% |

Figure 5A:
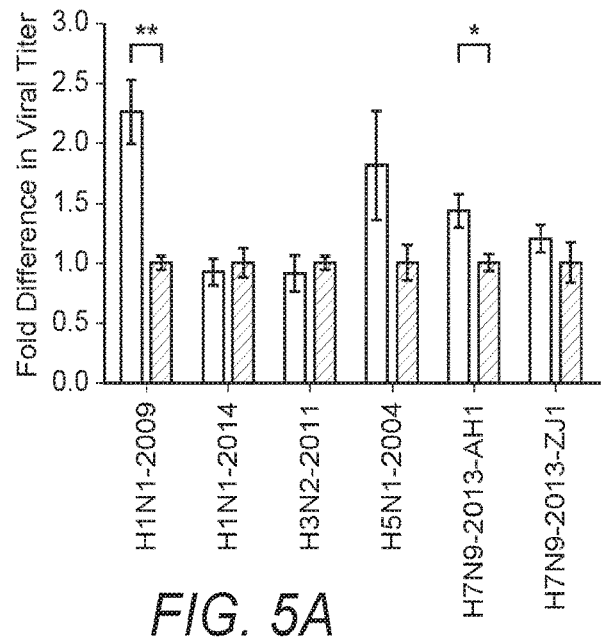
Figure 5B:
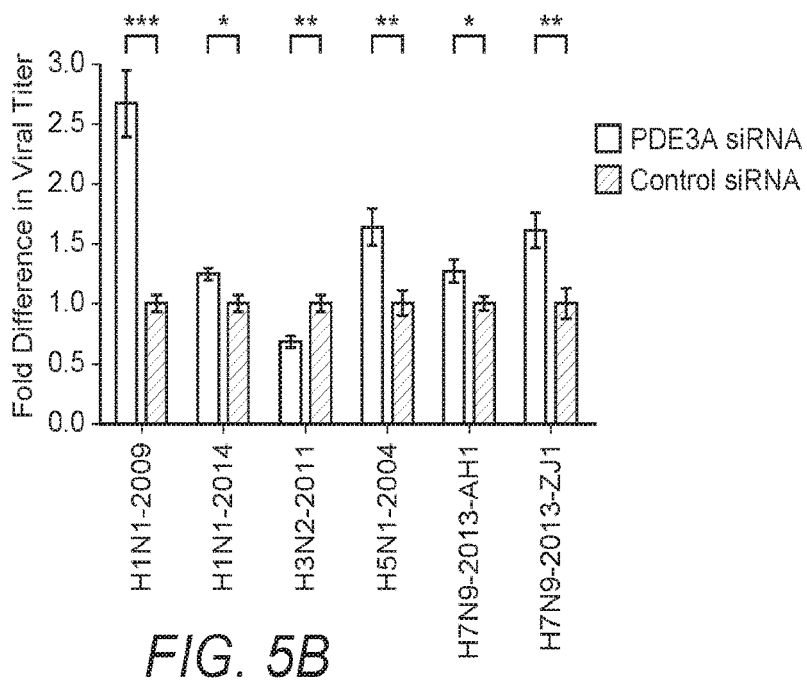

In multicycle growth assays, the viral titers of H1N1-2009 in PDE3A knockdown A549 cells were significantly higher at 24 hours (2.26-fold, P=0.001) and 48 hours (2.67-fold, P=0.0002) post-infection when compared with control cells (see FIGS. 5A and 5B).

The viral titers in the PDE3A knockdown cells were also significantly higher for H1N1-2014, H5N1-2004, H7N9-2013-AH1 and H7N9-2013-ZJ1 at 48 hours post-infection. However, the viral titer of H3N2-2011 was significantly lower at 48 hours post-infection for PDE3A knockdown cells than that of control cells (0.69-fold, P=0.0048).

Figure 5C:
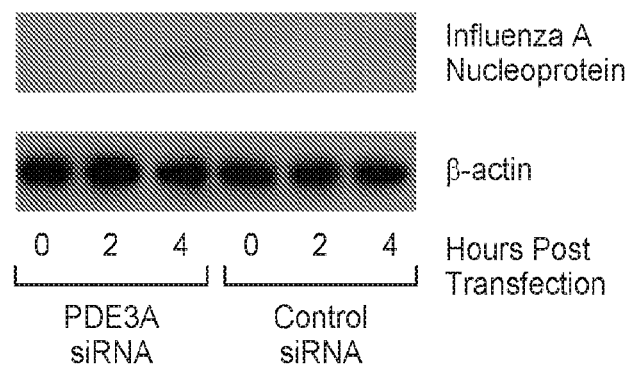

To further confirm the effect of PDE3A on viral replication, influenza A nucleoprotein expression in A549 cells after H1N1-2009 infection was determined. At 4 hours post-infection, influenza nucleoprotein expression was significantly enhanced in PDE3A-knockdown A549 cells than that of control siRNA-transfected A549 cells (see FIG. 5C).

Figure 6A:
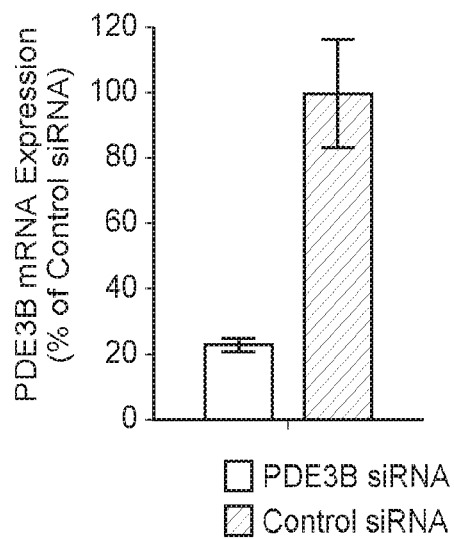
Figure 6B:
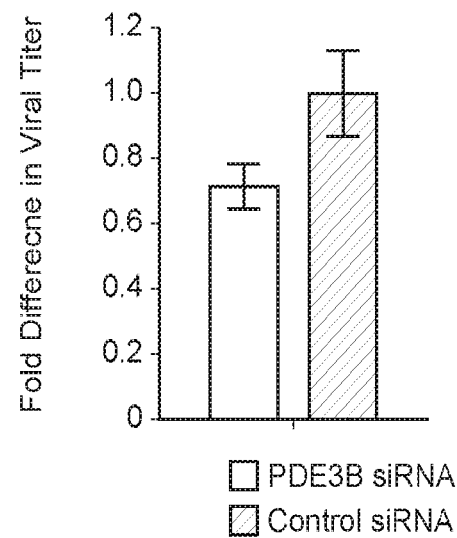
Figure 7A:
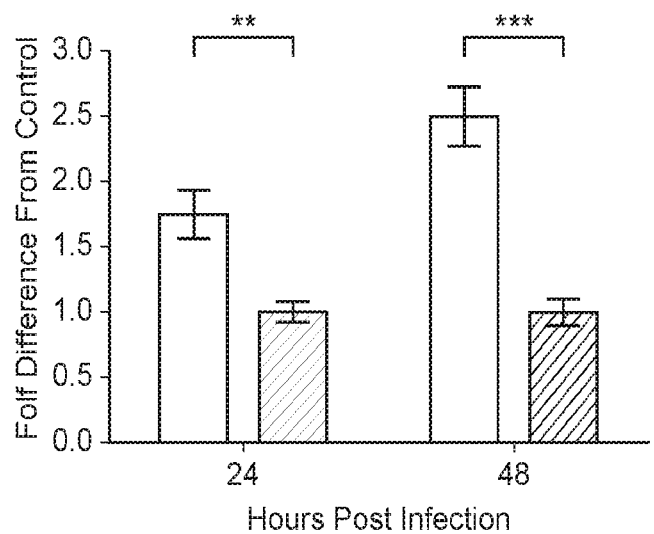
Figure 7B:
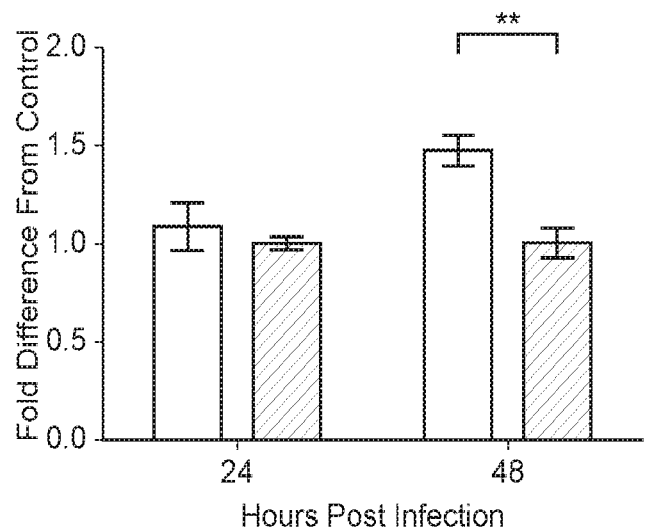

Since the protein structure of PDE3B is similar to that of PDE3A, the affects of siRNA knockdown of PDE3B on viral replication were determined. Importantly, there was no significant difference in the viral titers at 48 hours post-infection when A549 cells with PDE3B knockdown and control cells (see FIG. 6), indicating the specific effect of PDE3A even compared to a closely homologous PDE3B.

Figure 4A:
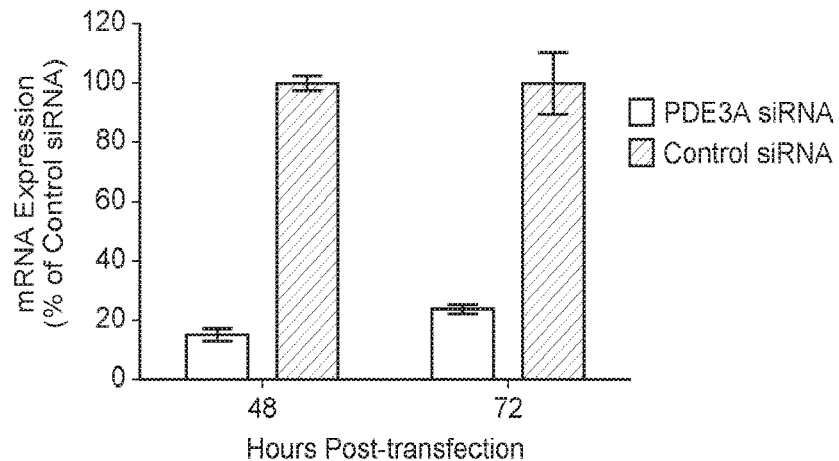
Figure 4B:
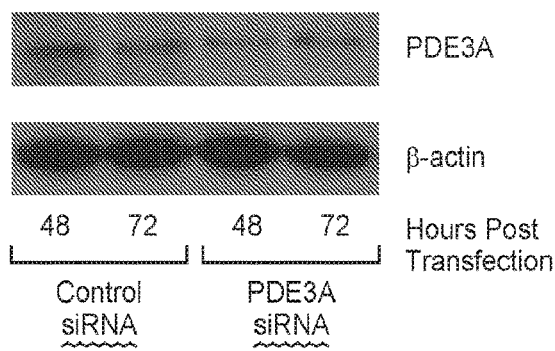

PDE3A knockdown and cytokine expression during influenza virus infection: The effect of PDE3A knockdown on cytokine and chemokine expression after H1N1-2009 infection of A549 cells was determined by RT-qPCR. PDE3A knockdown led to significant increased mRNA expression of IL-6 and IL-32 in the cell lysate (FIG. 4). However, there was no significant difference in the mRNA expression of IL10, TNF-α, IP-10, and IFN-0 between PDE3A knockdown A549 cells and control cells (data not shown).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

1. To K K, Chan J F, Chen H, Li L, Yuen K Y. The emergence of influenza A H7N9 in human beings 16 years after influenza A H5N1: a tale of two cities. Lancet Infect Dis 2013; 13:809-21.
2. Cheng V C, To K K, Tse H, Hung I F, Yuen K Y. Two years after pandemic influenza A/2009/H1N1: what have we learned? Clin Microbiol Rev 2012; 25:223-63.
3. Muthuri S G, Venkatesan S, Myles P R, et al. Effectiveness of neuraminidase inhibitors in reducing mortality in patients admitted to hospital with influenza A H1N1 pdm09 virus infection: a meta-analysis of individual participant data. The lancet Respiratory medicine 2014; 2:395-404.
4. Hurt A C, Chotpitayasunondh T, Cox N J, et al. Antiviral resistance during the 2009 influenza A H1N1 pandemic: public health, laboratory, and clinical perspectives. Lancet Infect Dis 2012; 12:240-8.
5. Hung I F, To K K, Lee C K, et al. Hyperimmune I V immunoglobulin treatment: a multicenter double-blind randomized controlled trial for patients with severe 2009 influenza A(H1N1) infection. Chest 2013; 144:464-73.
6. Hung I F, To K K, Lee C K, et al. Convalescent plasma treatment reduced mortality in patients with severe pandemic influenza A (H1N1) 2009 virus infection. Clin Infect Dis 2011; 52:447-56
7. Debing Y, Neyts J, Delang L. The future of antivirals: broad-spectrum inhibitors. Curr Opin Infect Dis 2015; 28:596-602.
8. Watanabe T, Kawaoka Y. Influenza virus-host interactomes as a basis for antiviral drug development. Curr Opin Virol 2015; 14:71-8.
9. Moss R B, Hansen C, Sanders R L, Hawley S, Li T, Steigbigel R T. A phase I I study of DAS181, a novel host directed antiviral for the treatment of influenza infection. J Infect Dis 2012; 206:1844-51.
10. Haffizulla J, Hartman A, Hoppers M, et al. Effect of nitazoxanide in adults and adolescents with acute uncomplicated influenza: a double-blind, randomised, placebo-controlled, phase 2b/3 trial. Lancet Infect Dis 2014; 14:609-18.
11. Blaising J, Polyak S J, Pecheur E I. Arbidol as a broad-spectrum antiviral: an update. Antiviral Res 2014; 107:84-94.
12. To K K, Mok K Y, Chan A S, et al. Mycophenolic acid, an immunomodulator, has potent and broad-spectrum in vitro antiviral activity against pandemic, seasonal and avian influenza viruses affecting humans. J Gen Virol 2016; 10.1099/jgv.0.000512.
13. Kollmus H, Wilk E, Schughart K. Systems biology and systems genetics—novel innovative approaches to study host-pathogen interactions during influenza infection. Curr Opin Virol 2014; 6:47-54.
14. To K K, Zhou J, Chan J F, Yuen K Y. Host genes and influenza pathogenesis in humans: an emerging paradigm. Curr Opin Virol 2015; 14:7-15.
15. To K K, Zhou J, Song Y Q, et al. Surfactant protein B gene polymorphism is associated with severe influenza. Chest 2014; 145:1237-43.
16. Zhou J, To K K, Dong H, et al. A functional variation in CD55 increases the severity of 2009 pandemic H1N1 influenza A virus infection. J Infect Dis 2012; 206:495-503.
17. Chen Y, Zhou J, Cheng Z, et al. Functional variants regulating LGALS1 (Galectin 1) expression affect human susceptibility to influenza A(H7N9). Sci Rep 2015; 5:8517.
18. Cheng Z, Zhou J, To K K, et al. Identification of TMPRSS2 as a Susceptibility Gene for Severe 2009 Pandemic A(H1N1) Influenza and A(H7N9) Influenza. J Infect Dis 2015; 212:1214-21.
19. To K K, Hung I F, Li I W, et al. Delayed clearance of viral load and marked cytokine activation in severe cases of pandemic H1N1 2009 influenza virus infection. Clin Infect Dis 2010; 50:850-9.
20. Genomes Project C, Auton A, Brooks L D, et al. A global reference for human genetic variation. Nature 2015; 526:68-74.
21. Chen Y, Liang W, Yang S, et al. Human infections with the emerging avian influenza A H7N9 virus from wet market poultry: clinical analysis and characterisation of viral genome. Lancet 2013; 381:1916-25.
22. To K K, Lau C C, Woo P C, et al. Human H7N9 virus induces a more pronounced pro-inflammatory cytokine but an attenuated interferon response in human bronchial epithelial cells when compared with an epidemiologically-linked chicken H7N9 virus. Virol J 2016; 13:42.
23. Lakics V, Karran E H, Boess F G. Quantitative comparison of phosphodiesterase mRNA distribution in human brain and peripheral tissues. Neuropharmacology 2010; 59:367-74.
24. Li C, Li C, Zhang A J, et al. Avian influenza A H7N9 virus induces severe pneumonia in mice without prior adaptation responds to a combination of zanamivir and COX-2 inhibitor. PLoS One 2014; 9:e107966.
25. Thapa D, Meng P, Bedolla R G, Reddick R L, Kumar A P, Ghosh R. NQO1 suppresses N F-kappaB-p300 interaction to regulate inflammatory mediators associated with prostate tumorigenesis. Cancer Res 2014; 74:5644-55.
26. Ahmad F, Degerman E, Manganiello V C. Cyclic nucleotide phosphodiesterase 3 signaling complexes. Horm Metab Res 2012; 44:776-85.
27. Mata M, Martinez I, Melero J A, Tenor H, Cortijo J. Roflumilast inhibits respiratory syncytial virus infection in human differentiated bronchial epithelial cells. PLoS One 2013; 8:e69670.
28. Bol S M, Booiman T, Bunnik E M, et al. Polymorphism in HIV-1 dependency factor PDE8A affects mRNA level and HIV-1 replication in primary macrophages. Virology 2011; 420:32-42.
29. Ding B, Abe J, Wei H, et al. Functional role of phosphodiesterase 3 in cardiomyocyte apoptosis: implication in heart failure. Circulation 2005; 111:2469-76.
30. Bao S, Zhou X, Zhang L, et al. Prioritizing genes responsible for host resistance to influenza using network approaches. BMC Genomics 2013; 14:816.
31. Ludwig S. Targeting cell signalling pathways to fight the flu: towards a paradigm change in anti-influenza therapy. J Antimicrob Chemother 2009; 64:1-4.
32. Yates A, Akanni W, Amode M R, et al. Ensembl 2016. Nucleic Acids Res 2016; 44:D710-6
33. Consortium G T. Human genomics. The Genotype-Tissue Expression (GTEx) pilot analysis: multitissue gene regulation in humans. Science 2015; 348:648-60.
34. Maiga M, Ammerman N C, Maiga M C, et al. Adjuvant host-directed therapy with types 3 and 5 but not type 4 phosphodiesterase inhibitors shortens the duration of tuberculosis treatment. J Infect Dis 2013; 208:512-9.
35. Begum N, Hockman S, Manganiello V C. Phosphodiesterase 3A (PDE3A) deletion suppresses proliferation of cultured murine vascular smooth muscle cells (VSMCs) via inhibition of mitogen-activated protein kinase (MAPK) signaling and alterations in critical cell cycle regulatory proteins. J Biol Chem 2011; 286:26238-49.
36. Ehrhardt C, Ludwig S. A new player in a deadly game: influenza viruses and the PI3K/Akt signalling pathway. Cell Microbiol 2009; 11:863-71.
37. Park W S, Jung W K, Lee D Y, et al. Cilostazol protects mice against endotoxin shock and attenuates LPS-induced cytokine expression in RAW 264.7 macrophages via MAPK inhibition and NF-kappaB inactivation: not involved in cAMP mechanisms. Int Immunopharmacol 2010; 10:1077-85.
38. Wada T, Onogi Y, Kimura Y, et al. Cilostazol ameliorates systemic insulin resistance in diabetic db/db mice by suppressing chronic inflammation in adipose tissue via modulation of both adipocyte and macrophage functions. Eur J Pharmacol 2013; 707:120-9.
39. Bueltmann M, Kong X, Mertens M, et al. Inhaled milrinone attenuates experimental acute lung injury. Intensive Care Med 2009; 35:171-8.
40. Oishi H, Takano K, Tomita K, et al. Olprinone and colforsin daropate alleviate septic lung inflammation and apoptosis through CREB-independent activation of the Akt pathway. Am J Physiol Lung Cell Mol Physiol 2012; 303:L130-40.
41. Mokra D, Drgova A, Pullmann R, Sr., Calkovska A. Selective phosphodiesterase 3 inhibitor olprinone attenuates meconium-induced oxidative lung injury. Pulm Pharmacol Ther 2012; 25:216-22.
42. Turhan A H, Atici A, Muslu N, Polat A, Helvaci I. The effects of pentoxifylline on lung inflammation in a rat model of meconium aspiration syndrome. Exp Lung Res 2012; 38:250-5.
43. Sharma G, Champalal Sharma D, Hwei Fen L, et al. Reduction of influenza virus-induced lung inflammation and mortality in animals treated with a phosophodisestrase-4 inhibitor and a selective serotonin reuptake inhibitor. Emerg Microbes Infect 2013; 2:e54.

44. Witzenrath M, Gutbier B, Schmeck B, et al. Phosphodiesterase 2 inhibition diminished acute lung injury in murine pneumococcal pneumonia. Crit Care Med 2009; 37:584-90.
45. Maass P G, Aydin A, Luft F C, et al. PDE3A mutations cause autosomal dominant hypertension with brachydactyly. Nat Genet 2015; 47:647-53.
46. Kato N, Loh M, Takeuchi F, et al. Trans-ancestry genome-wide association study identifies 12 genetic loci influencing blood pressure and implicates a role for DNA methylation. Nat Genet 2015; 47:1282-93.
47. Boda H, Uchida H, Takaiso N, et al. A PDE3A mutation in familial hypertension and brachydactyly syndrome. J Hum Genet 2016; 10.1038/jhg.2016.32.
48. Penmatsa H, Zhang W, Yarlagadda S, et al. Compartmentalized cyclic adenosine 3',5'-monophosphate at the plasma membrane clusters PDE3A and cystic fibrosis transmembrane conductance regulator into microdomains. Mol Biol Cell 2010; 21:1097-110.
49. Gantner F, Gotz C, Gekeler V, Schudt C, Wendel A, Hatzelmann A. Phosphodiesterase profile of human B lymphocytes from normal and atopic donors and the effects of PDE inhibition on B cell proliferation. Br J Pharmacol 1998; 123:1031-8.
50. Gnirss K, Zmora P, Blazejewska P, et al. Tetherin sensitivity of influenza A viruses is strain specific: Role of hemagglutinin and neuraminidase. J Virol 2015; 10.1128/JVI.00615-15.

What is claimed is:

1. A method of treating influenza in an individual, comprising:
   i) obtaining a sample from the individual;
   ii) determining that the individual carries a PDE3A mutation associated with severe influenza disease, wherein the mutation comprises one or more of T at rs7314545, T at rs6487131, and G at rs6487132; and
   iii) treating the individual determined to carry the PDE3A mutation(s) with an antiviral compound effective against influenza.

2. The method of claim 1, wherein the sample is selected from the group consisting of blood, saliva, a nasal swab, and a cheek swab.

3. The method of claim 1, comprising performing a test characterizing a PDE3A gene product on at least a portion of the sample.

4. The method of claim 1, comprising a polynucleotide amplification step.

5. The method of claim 1, comprising an immunochemical assay.

6. The method of claim 1, wherein the PDE3A mutation results in reduced PDE3A gene product activity.

7. The method of claim 1, wherein the PDE3A mutation results in reduced PDE3A gene transcription.

8. The method of claim 1, wherein the PDE3A mutation results in reduced PDE3A gene translation.

9. The method of claim 1, wherein the PDE3A mutation results in an impaired capacity for viral clearance and higher viral replication during an influenza infection compared to a control without the PDE3A mutation.

10. The method of claim 1, wherein the PDE3A mutation results in elevated proinflammatory cytokine expression during an influenza infection compared to a control without the PDE3A mutation.

11. The method of claim 10, wherein the proinflammatory cytokine is selected from the group consisting of IL-6 and IL-32.

12. The method of claim 1, wherein the PDE3A mutation results in reduced antiviral and anti-inflammatory activities during an influenza infection compared to a control without the PDE3A mutation.

* * * * *

SEQUENCE LISTING

```
<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: PDE3A-Forward primer

<400> SEQUENCE: 1
gatgataaat acggatgtct gtc                                          23

<210> SEQ ID NO 2
<211> LENGTH: 19
<212> TYPE: DNA
<213> ORGANISM: Artificial Sequence
<220> FEATURE:
<223> OTHER INFORMATION: PDE3A-Reverse primer

<400> SEQUENCE: 2
accgcctgag gagcactag                                               19

<210> SEQ ID NO 3
<211> LENGTH: 25
<212> TYPE: DNA
<213> ORGANISM: Artificial Sequence
<220> FEATURE:
<223> OTHER INFORMATION: PDE3B-Forward primer

<400> SEQUENCE: 3
aaaggggata gaaaacttaa caagg                                        25

<210> SEQ ID NO 4
<211> LENGTH: 22
<212> TYPE: DNA
<213> ORGANISM: Artificial Sequence
<220> FEATURE:
<223> OTHER INFORMATION: PDE3B-Reverse primer

<400> SEQUENCE: 4
caggtagcaa tcctgaagtt cc                                           22

<210> SEQ ID NO 5
<211> LENGTH: 19
<212> TYPE: DNA
<213> ORGANISM: Artificial Sequence
<220> FEATURE:
<223> OTHER INFORMATION: PDE4A-Forward primer

<400> SEQUENCE: 5
ttcacggacc tggagattc                                               19
```

<210> SEQ ID NO 6
<211> LENGTH: 19
<212> TYPE: DNA
<213> ORGANISM: Artificial Sequence
<220> FEATURE:
<223> OTHER INFORMATION: PDE4A-Reverse primer

<400> SEQUENCE: 6
tgaggaactg gttggagac                                                    19

<210> SEQ ID NO 7
<211> LENGTH: 23
<212> TYPE: DNA
<213> ORGANISM: Artificial Sequence
<220> FEATURE:
<223> OTHER INFORMATION: PDE4B-Forward primer

<400> SEQUENCE: 7
caagcctaaa caatacaagc atc                                               23

<210> SEQ ID NO 8
<211> LENGTH: 24
<212> TYPE: DNA
<213> ORGANISM: Artificial Sequence
<220> FEATURE:
<223> OTHER INFORMATION: PDE4B-Reverse primer

<400> SEQUENCE: 8
tgagaatatc cagccacatt aaag                                              24

<210> SEQ ID NO 9
<211> LENGTH: 18
<212> TYPE: DNA
<213> ORGANISM: Artificial Sequence
<220> FEATURE:
<223> OTHER INFORMATION: PDE4C-Forward primer

<400> SEQUENCE: 9
cacctggctg tgggcttc                                                     18

<210> SEQ ID NO 10
<211> LENGTH: 18
<212> TYPE: DNA
<213> ORGANISM: Artificial Sequence
<220> FEATURE:
<223> OTHER INFORMATION: PDE4C-Reverse primer

<400> SEQUENCE: 10
actcagtcgc tgcttggc                                                     18

<210> SEQ ID NO 11
<211> LENGTH: 24
<212> TYPE: DNA
<213> ORGANISM: Artificial Sequence
<220> FEATURE:
<223> OTHER INFORMATION: PDE4D-Forward primer

<400> SEQUENCE: 11
ctactggctg atttgaagac tatg                                              24

<210> SEQ ID NO 12
<211> LENGTH: 19
<212> TYPE: DNA
<213> ORGANISM: Artificial Sequence
<220> FEATURE:

```
<223> OTHER INFORMATION: PDE4D-Reverse primer

<400> SEQUENCE: 12
gctggagagg ctttgttgg                                                   19

<210> SEQ ID NO 13
<211> LENGTH: 21
<212> TYPE: DNA
<213> ORGANISM: Artificial Sequence
<220> FEATURE:
<223> OTHER INFORMATION: PDE8A-Forward primer

<400> SEQUENCE: 13
atgtttgctc gctttggaat c                                                21

<210> SEQ ID NO 14
<211> LENGTH: 24
<212> TYPE: DNA
<213> ORGANISM: Artificial Sequence
<220> FEATURE:
<223> OTHER INFORMATION: PDE8A-Reverse primer

<400> SEQUENCE: 14
cagaatgtgt agaattgtgg tagg                                             24

<210> SEQ ID NO 15
<211> LENGTH: 20
<212> TYPE: DNA
<213> ORGANISM: Artificial Sequence
<220> FEATURE:
<223> OTHER INFORMATION: GAPDH-Forward primer

<400> SEQUENCE: 15
attccaccca tggcaaattc                                                  20

<210> SEQ ID NO 16
<211> LENGTH: 20
<212> TYPE: DNA
<213> ORGANISM: Artificial Sequence
<220> FEATURE:
<223> OTHER INFORMATION: GAPDH-Reverse primer

<400> SEQUENCE: 16
cgctcctgga agatggtgat                                                  20

<210> SEQ ID NO 17
<211> LENGTH: 20
<212> TYPE: DNA
<213> ORGANISM: Artificial Sequence
<220> FEATURE:
<223> OTHER INFORMATION: IL-6-Forward primer

<400> SEQUENCE: 17
ggctgcagga catgacaact                                                  20

<210> SEQ ID NO 18
<211> LENGTH: 20
<212> TYPE: DNA
<213> ORGANISM: Artificial Sequence
<220> FEATURE:
<223> OTHER INFORMATION: IL-6-Reverse primer

<400> SEQUENCE: 18
atctgaggtg cccatgctac                                                  20
```

```
<210> SEQ ID NO 19
<211> LENGTH: 24
<212> TYPE: DNA
<213> ORGANISM: Artificial Sequence
<220> FEATURE:
<223> OTHER INFORMATION: IL-32-Forward primer

<400> SEQUENCE: 19
aatcaggacg tggacaggtg atgt                                                24

<210> SEQ ID NO 20
<211> LENGTH: 24
<212> TYPE: DNA
<213> ORGANISM: Artificial Sequence
<220> FEATURE:
<223> OTHER INFORMATION: IL-32-Reverse primer

<400> SEQUENCE: 20
tgctcctcat aataagccgc cact                                                24

<210> SEQ ID NO 21
<211> LENGTH: 20
<212> TYPE: DNA
<213> ORGANISM: Artificial Sequence
<220> FEATURE:
<223> OTHER INFORMATION: TNF-alpha-Forward primer

<400> SEQUENCE: 21
caaggacagc agaggaccag                                                     20

<210> SEQ ID NO 22
<211> LENGTH: 20
<212> TYPE: DNA
<213> ORGANISM: Artificial Sequence
<220> FEATURE:
<223> OTHER INFORMATION: TNF-alpha-Reverse primer

<400> SEQUENCE: 22
tggcgtctga gggttgtttt                                                     20

<210> SEQ ID NO 23
<211> LENGTH: 20
<212> TYPE: DNA
<213> ORGANISM: Artificial Sequence
<220> FEATURE:
<223> OTHER INFORMATION: IP-10-Forward primer

<400> SEQUENCE: 23
agcagaggaa cctccagtct                                                     20

<210> SEQ ID NO 24
<211> LENGTH: 20
<212> TYPE: DNA
<213> ORGANISM: Artificial Sequence
<220> FEATURE:
<223> OTHER INFORMATION: IP-10-Reverse primer

<400> SEQUENCE: 24
atgcaggtac agcgtacagt                                                     20

<210> SEQ ID NO 25
<211> LENGTH: 16
<212> TYPE: DNA
<213> ORGANISM: Artificial Sequence
<220> FEATURE:
<223> OTHER INFORMATION: IFN-beta-Forward primer
```

```
<400> SEQUENCE: 25
gccgcattga ccatct                                                  16

<210> SEQ ID NO 26
<211> LENGTH: 18
<212> TYPE: DNA
<213> ORGANISM: Artificial Sequence
<220> FEATURE:
<223> OTHER INFORMATION: IFN-beta-Reverse primer

<400> SEQUENCE: 26
cacagtgact gtactcct                                                18
```